United States Patent

Rose et al.

[11] Patent Number: 5,231,979
[45] Date of Patent: Aug. 3, 1993

[54] HUMIDIFIER FOR CPAP DEVICE

[75] Inventors: Fred Rose, Overland Park; Lisa Kidd, Leawood; Roger Dolida, Overland Park, all of Kans.

[73] Assignee: Puritan-Bennett Corporation, Lenexa, Kans.

[21] Appl. No.: 835,589

[22] Filed: Feb. 14, 1992

[51] Int. Cl.⁵ .................... A61M 15/00; A61M 11/00
[52] U.S. Cl. ........................ 128/204.14; 128/200.24; 128/203.12
[58] Field of Search .................. 128/203.12, 204.13, 128/204.14, 200.11, 200.24; 261/DIG. 4, DIG. 15, DIG. 34, DIG. 65; 237/78; 236/44 R

[56] References Cited

U.S. PATENT DOCUMENTS

| | | | |
|---|---|---|---|
| 2,710,178 | 6/1955 | Froelich | 261/DIG. 34 X |
| 3,043,573 | 7/1962 | Chandler | 261/DIG. 34 X |
| 4,014,382 | 3/1977 | Heath | 261/DIG. 65 X |
| 4,060,576 | 11/1977 | Grant | 261/DIG. 65 X |
| 4,152,379 | 5/1979 | Suhr | 261/142 |
| 4,461,735 | 7/1984 | Wirt | 261/104 |

FOREIGN PATENT DOCUMENTS

| | | | |
|---|---|---|---|
| 3627351 | 2/1988 | Fed. Rep. of Germany | 128/204.13 |
| 2176313 | 12/1986 | United Kingdom | 128/203.12 |
| 2177007 | 1/1987 | United Kingdom | 128/203.12 |

*Primary Examiner*—Edgar S. Burr
*Assistant Examiner*—Eric P. Raciti
*Attorney, Agent, or Firm*—Hovey, Williams, Timmons & Collins

[57] ABSTRACT

A humidifier (10) is provided which includes a body (16) defining a plenum (32) for receiving air and a quantity of water therewithin, said body (16) further presenting a tubular inlet (18) and a-tubular outlet (20), and a baffle (34) for directing the flow of air therethrough, said body (16) being integrally formed. A shelf (58) is provided adjacent the outlet (20) for minimizing the effect of waves generated by the flow of circulating air and inhibiting the discharge of water droplets through the outlet (20) which would otherwise be carried by the circulating air. The body (16) is preferably provided with a U-shaped sidewall (55) with the baffle (34) positioned between first and second sidewalls (36, 38) thereof so that the air introduced through the inlet (18) is directed in a U-shaped flow path to enhance humidification before it is exhausted through the outlet (20). The baffle (34) preferably extends between the upper panel (40) and the lower panel (42) of the body (16) to provide strength and prevent the collapse of the humidifier body when heavy objects are placed thereon, as well as ballooning of the body (16) caused by internal pressurization.

6 Claims, 2 Drawing Sheets

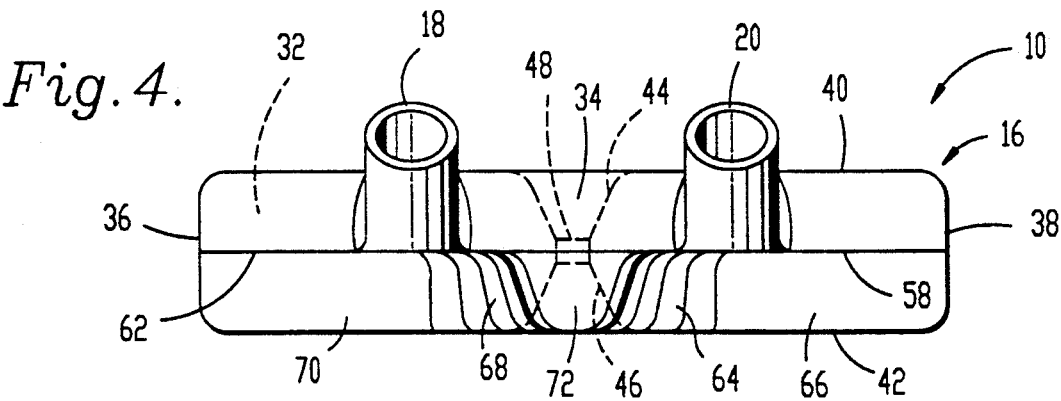
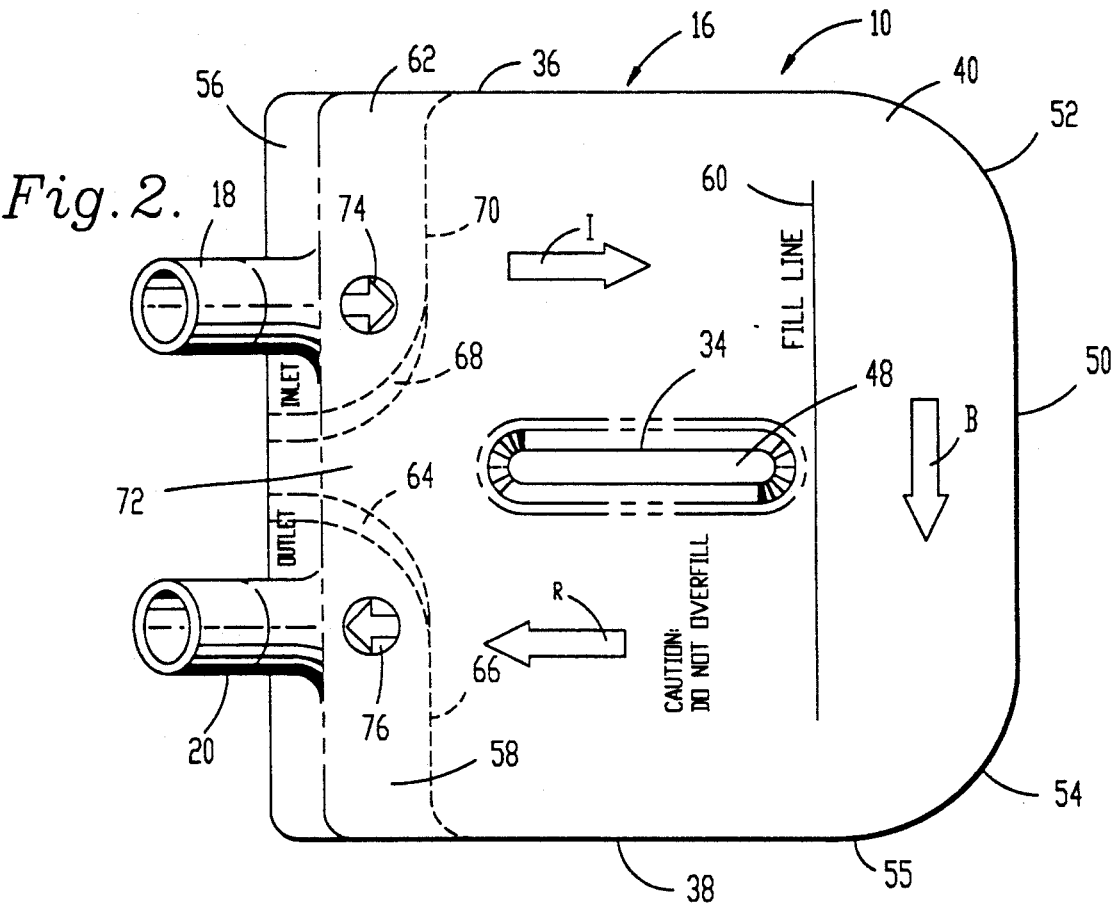
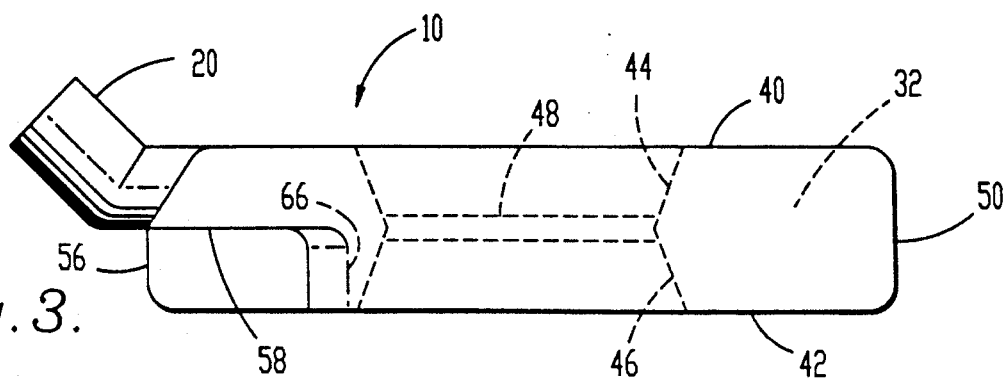

HUMIDIFIER FOR CPAP DEVICE

BACKGROUND OF THE INVENTION

1. Field of the Invention

A humidifier for a CPAP device presents an internal baffle integrally formed with, extending between and interconnecting upper and lower panels of the humidifier to direct the flow of air therethrough and enhance the structural integrity of the humidifier. The humidifier also includes a shelf adjacent the outlet of the humidifier to minimize wave formation and the discharge of water droplets carried by the air circulating therethrough.

2. Description of the Prior Art

Sleep Apnea Syndrome is a disorder characterized by cessation of breathing and frequent awakenings during sleep. One class of sleep apnea is obstructive sleep apnea, which is characterized by the obstruction of the person's upper airway resulting in interference with breathing during sleep In order to treat obstructive sleep apnea, Continuous Positive Airway Pressure (CPAP) devices have been developed to deliver air under constant positive pressure to the nasal passages during sleep. These devices are frequently successful in treating sleep deprivation due to obstructive sleep apnea.

In order to prevent drying of the breathing passages during the administration of CPAP, it is desirable to humidify the air supplied to the person using such devices This may be accomplished by providing a humidifier which is essentially a bottle containing a quantity of water over which the air under pressure passes before being delivered to the user. The user partially fills the bottle with water, and the air is circulated within the bottle to pass over the surface of the water and absorb moisture therefrom.

One problem with prior art humidifiers has been the expense connected with manufacturing these bottles. One such humidifier, made by Respironics, Inc. of Monroeville, Pa., requires multiple parts which are time-consuming to assemble. These parts have the potential to leak at the seams or joints therebetween. Parts such as a gasket may become torn. Another problem encountered with the use of certain humidifiers, especially shallow, low-profile types, is the passage of water droplets out of the outlet of the humidifier borne by the circulating air. Such droplets may develop because of the tendency of the circulating air to form waves on the water contained therein, the air stripping droplets from the waves and spraying the droplets through the outlet. Airborne droplets of water may ultimately reach the user during sleep and potentially awaken the user. Finally, prior humidifiers have been subject to breakage during rough handling.

Thus, there has developed a real need for a humidifier which is economical to manufacture yet strong and lightweight, which circulates the air therewithin to achieve maximum humidification, and inhibits the passage of water droplets through the outlet.

SUMMARY OF THE INVENTION

These and other problems have been solved by the CPAP humidifier in accordance with the present invention, which presents a humidifier which is economical to manufacture, easy to use, durable, and promotes the circulation of humidified air therethrough while minimizing the generation of water droplets to be carried by the circulating air.

Broadly speaking, the present invention concerns a body presenting an inlet and an outlet and having a shelf adjacent the outlet which serves to divert and dissipate waves in the water contained within the body caused by the flow of circulating air. The body is preferably integrally formed of thermoplastic materials and incorporates one or more baffles. The baffle promotes the flow of air therethrough in a U-shaped or other appropriate indirect path, as well as providing rigidity and structural reinforcement between the opposed, upper and lower panels of the body. The baffle is formed integrally with the body and extends between the upper and lower panels to define a support pillar which resists compression between the panels and ballooning when the panels are subjected to internal pressure.

The shelf adjacent the outlet is preferably provided with an arcuate ledge for dissipating waves and diverting the waves away from the outlet. The shelf is configured to extend above the operating level of the water within the body and thus provides a relatively dry surface adjacent the outlet. A platform is similarly provided adjacent but spaced relative to the inlet to define a trough therebetween. The shelf and the platform have respectively an arcuate ledge and arcuate rim facing each other in opposed relationship. The body presents a generally rectangular configuration in plan with side and back walls connected by arcuate corners which, together with the internal baffle, serve to provide the generally U-shaped flow path for the air circulating within the plenum defined by the surrounding body. Air enters the humidifier, absorbs humidity from the water contained therein, and humidified air is exhausted through the outlet. The inlet and outlet fittings are substantially symmetrical and preferably located on the same side of the humidifier body so that the exhausted humidified air flows in a generally parallel but opposed direction to the air entering through the intake.

Because the humidifier hereof is formed integrally without the need for screws, seals, gaskets or the like, manufacturing costs are minimized. In addition, the humidifier hereof is essentially leak-free because there are no seams or joints to seal. Finally, the resulting humidifier is very strong and resistant to damage from handling.

BRIEF DESCRIPTION OF THE DRAWINGS

FIG. 2 is a top plan view of the humidifier hereof;

FIG. 3 is a side elevation view of the humidifier hereof; and

FIG. 4 is an end elevation view of the humidifier hereof.

DESCRIPTION OF THE PREFERRED EMBODIMENT

Figure 1:
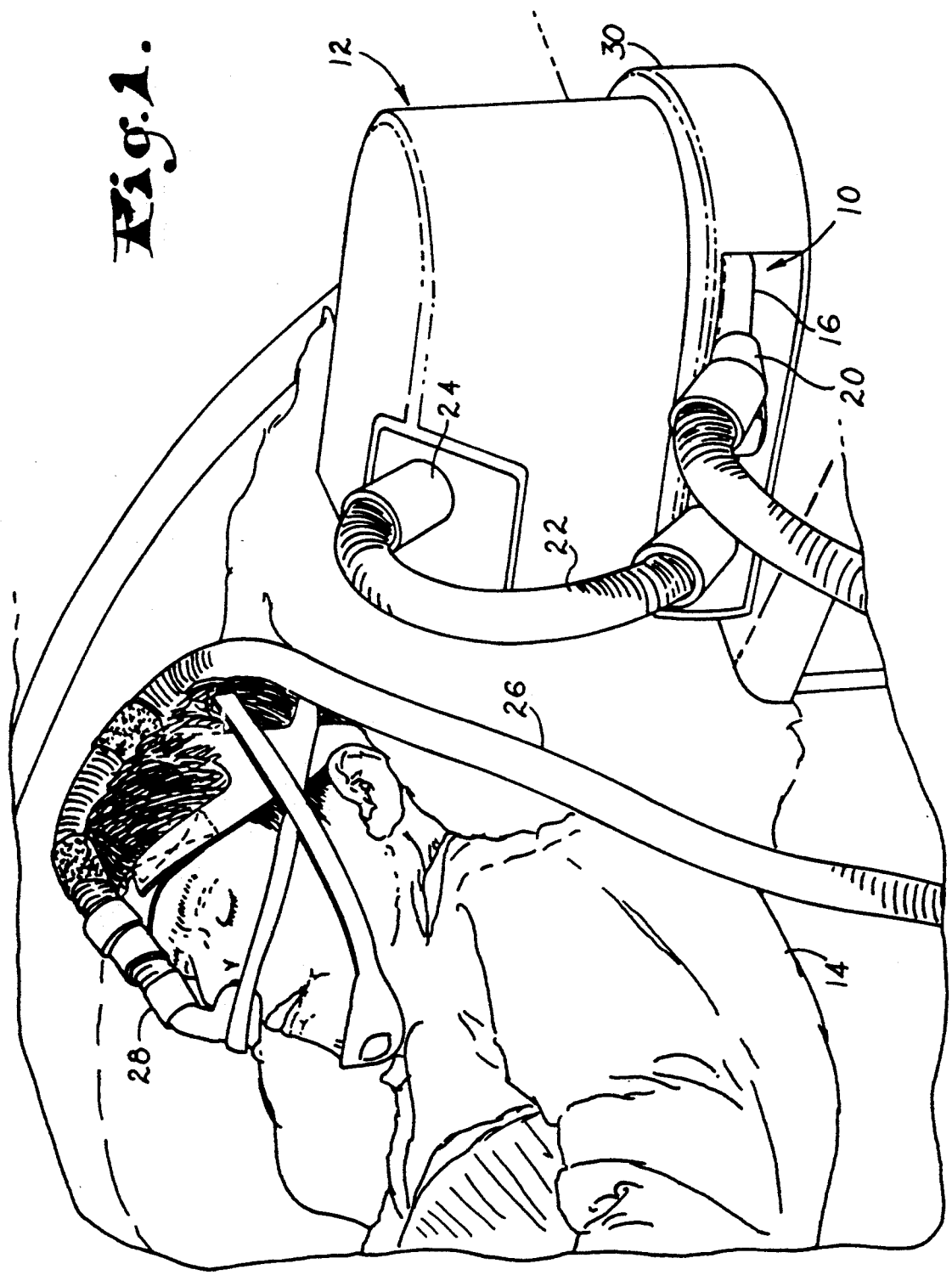
FIG. 1 is a fragmentary perspective view of a humidifier especially adapted for use in conjunction with continuous positive airway pressure (CPAP) devices which humidifies air prior to delivery to a sleep apnea patient.

Referring now to the drawing, a humidifier 10 in accordance with the present invention is shown in FIG. 1 operatively connected to a CPAP device 12 for delivering air under pressure to the nasal airway of a patient 14. The humidifier 10 (see FIG. 2) includes a body 16 providing an inlet 18 and an outlet 20. The inlet 18 is connected by tube 22 to the air outlet 24 of the CPAP device. Positive air pressure is supplied by the CPAP device through the air outlet 24 thereof. The pressurized air from the CPAP device 12 is thus circulated through the humidifier 10 for subsequent delivery to the patient through air hose 26 to mask 28. As may be seen in FIG. 1, the CPAP device is configured to rest upon a humidifier housing 30 with the humidifier 10 hereof received therewithin. A CPAP device useful with the humidifier 10 of the present invention is Companion ® 318 Nasal CPAP System available from Puritan Bennett of Lenexa, Kans., as well as the associated mask, tubing, hoses and housing 30 furnished therewith.

In greater detail, the humidifier 10 includes inlet 18 and outlet 20 which are in the form of tubular extensions adapted for receiving tube 22 and hose 26 respectively thereon. Body 16 defines a plenum 32 therewithin with which tubular inlet 18 and tubular outlet 20 fluidically communicate. In addition, body 16 is formed to define an elongate baffle 34 located generally intermediate normally upright first side wall 36 and normally upright second side wall 38 thereby defining respective first incoming and second return legs of the U-shaped air circulation path. The humidifier 10 is preferably formed of a thermoplastic synthetic resin material such as clear polycarbonate which is dishwasher safe, autoclavable, and can withstand severe handling. The clear polycarbonate material allows the user to easily view the level of the water received within the plenum 32.

Body 16 further includes an upper panel 40 and a lower panel 42 each of which are generally planar, parallel and opposed to one another. Baffle 34 extends between upper panel 40 and lower panel 42 and is formed by depressions 44 and 46 respectively extending into the plenum 32. Depressions 44 and 46 join together at tackoff 48 whereby baffle 34 forms a fluid-impermeable central pillar essentially intermediate first and second sidewalls 36 and 38. Body 16 further includes normally upright back wall 50 presenting arcuate corners 52 and 54. First and second sidewalls 36 and 38, back wall 50, and corners 52 and 54 comprise to form generally U-shaped surrounding wall 55.

Front end wall 56 is generally opposed to back wall 50 with inlet 18 and outlet 20 extending upwardly and outwardly therefrom. A shelf 58 is integrally formed with the body 16 and extends rearwardly toward back wall 50 from the lower portion of front end wall 56 adjacent tubular outlet 20. Shelf 58 is spaced upwardly from lower panel 42 a sufficient distance so that when the humidifier 10 is placed in horizontal position as shown in FIGS. 3 and 4 after plenum 32 has been filled with water to the fill line indicia 60 shown in FIG. 2 (with front wall 56 in an uppermost orientation), the water contained within plenum 32 does not extend over and onto shelf 58. Similarly, a platform 62 is defined by body 16 adjacent inlet 18, and is spaced upwardly from lower panel 42 in the same manner as shelf 58.

Shelf 58 is provided an arcuate ledge 64 which extends forwardly from shelf wall 66 toward front end wall 56. Similarly, platform 62, which is spaced from shelf 58 and shown in FIG. 2, is provided with an arcuate rim 68 which extends forwardly from platform wall 70 toward front end wall 56. A trough 72 is thus defined between ledge 64 and rim 68.

The humidifier 10 is preferably integrally formed by molding polycarbonate or other synthetic resin material. Extrusion blow molding produces a very satisfactory humidifier 10, although other manufacturing methods known to those skilled in the art such as rotational molding and injection blow molding can be used. The resulting humidifier 10 presents a transparent or translucent body through which the user can ascertain the water level, is strong and resistant to compression or bulging due to internal pressure, and presents no openings or seams through which water can leak.

In use, the body is first placed in a generally upright position with tubular inlet 18 and tubular outlet 20 uppermost and water is poured into plenum 32 until it reaches fill line indicia 60. The humidifier is filled only to this level to prevent water from extending over the shelf 58 and platform 62 when the humidifier 10 is placed in its usual, flat position as shown in FIGS. 3 and 4, and also so that only enough water is received within the plenum for a single night's use, which is beneficial for reducing the risk of infection. The humidifier 10 is then reoriented into the horizontal position shown in FIGS. 3 and 4 and placed within housing 30 as shown in FIG. 1. Tube 22 then connects the air outlet of the CPAP device 12 with the inlet 18 of the humidifier 10, while hose 26 connects the outlet 20 of the humidifier 10 with the mask 28 leading to the user's nasal passages.

Upon activation of the CPAP device 12, inlet 18 receives an intake of air in the direction generally illustrated by the arrow indicia 74. The air is circulated in a generally U-shaped pattern including an incoming leg I between baffle 34 and first side wall 36, bight leg B between back wall 50 and baffle 34, and then return leg R between baffle 34 and second side wall 38 before passing through outlet 20 in the direction generally indicated by arrow indicia 76. As the air passes through the plenum 32 and over the water received therein, it becomes humidified. Because the air is moving, it tends to generate small waves on the surface of the water within the plenum 32. Ledge 64 is provided with a generous radius whereby the waves are diverted and dissipated into trough 72. Thus, the wave height at the shelf 58 adjacent the outlet 20 is controlled by providing a return for the excess pool of water to flow toward the inlet 18, with rim 68 additionally controlling the waves by dispersing the wave action into the water between first side wall 36 and baffle 34. Platform 62 also spaces the water within the plenum 32 away from the inlet 18 so that the velocity of the flow of air engaging the surface of the water is thus reduced. The shelf 58 and the platform 62 promote controlled turbulence of the pool of water within the plenum 32 and enhances humidification without allowing high velocity air streams from spraying droplets of water through the outlet without increasing back pressure.

Although the particular humidifier heretofore described is especially adapted for use in CPAP devices, the invention is not so limited. Broadly speaking, the principles of the invention can be used in the fabrication of humidifiers for virtually any breathing device where humidification is in order. In addition, while a single, central, integral baffle has been shown, which effectively defines a U-shaped airway path through the humidifier, other alternatives are possible For example, a pair of spaced apart baffle walls, together with an inlet and an outlet on opposite ends of the humidifier body, could be employed. This would generate an essentially S-shaped or serpentine airflow path through the humidifier. A unit could also be fabricated without any baffles whatsoever, but in this case it will be advantageous to provide respective shelves adjacent the inlet and the outlet. Inasmuch as the preferred humidifier body is integrally formed by extrusion blow molding or other techniques, those skilled in the art will appreciate that an integral handle could readily be provided. Furthermore, retention detents and/or apertures for receiving retaining devices could readily be provided. While the flattened, squat configuration of the present humidifier is preferred, wherein the top and bottom walls present a maximum dimension in the plane thereof which is substantially greater than the height of the body sidewall, other configurations are possible, e.g., use of top and bottom walls which are non-parallel. Finally, in the preferred form of the invention, the shelf and baffle structure are symmetrical about the axis of the humidifier. This is preferred in that if a user inadvertently reverses the inlet and outlet lines to the humidifier, the unit will still operate. However, it is not essential that humidifiers in accordance with the invention have such symmetry.

We claim:

1. In a humidifier for creating contact between an incoming air stream and a supply of water in order to produce a humidified air output stream, said humidifier having walls defining an air-water plenum chamber, including a top wall, an opposed bottom wall, and an upright sidewall joining said top and bottom walls, a tubular air input communicating with the chamber, and a tubular humidified air output spaced from said inlet and communicating with said chamber, said chamber being operable for holding a supply of water having a normal depth such that the upper surface of the water is beneath said input and output, the improvement which comprises:

an outlet shelf wall adjacent and beneath said outlet, said outlet shelf wall extending inwardly from said sidewall between said top and bottom walls and presenting an inner margin, said outlet shelf wall being located a distance above said bottom wall which is greater than the normal depth of said water supply; and an upright outlet ledge wall extending between and interconnecting said outlet shelf wall inner margin and said bottom wall, said outlet ledge wall being in contact with said water supply and oriented for dissipating waves within the water supply.

2. The humidifier of claim 1, said sidewall having a height substantially less than the length and width of said top and bottom walls so that the humidifier assumes a thin, low-profile configuration.

3. The humidifier of claim 1, said walls being formed as an integral composite body.

4. The humidifier of claim 1, including structure defining a baffle wall extending between and interconnecting said top and bottom walls, said baffle wall being located between said inlet and outlet for directing said incoming air stream around the baffle wall towards said outlet.

5. The humidifier of claim 1, including an inlet shelf wall adjacent and beneath said inlet, said inlet shelf wall extending inwardly from said sidewall between said top and bottom walls and presenting an inner margin, said inlet shelf wall being located a distance above said bottom wall which is greater than the normal depth of said water supply, an upright inlet ledge wall extending between and interconnecting said inlet shelf wall inner margin and said bottom wall, said inlet ledge wall being in contact with said water supply and oriented for dissipating waves within the water supply, said inlet and outlet shelf walls, and said inlet and outlet ledge walls, being in laterally spaced relationship to each other.

6. The humidifier of claim 5, said inlet and outlet ledge walls each being arcuate in plan configuration and each being tapered between the corresponding inner margins of said inlet and outlet shelf walls and said bottom wall.

* * * * *